(12) United States Patent
Senatore (10) Patent No.: US 9,144,436 B2
(45) Date of Patent: Sep. 29, 2015

(54) APPARATUS FOR HANGING DROP DETECTION OF EPIDURAL SPACE PENETRATION

(71) Applicant: Thomas A. Senatore, Newton, NJ (US)

(72) Inventor: Thomas A. Senatore, Newton, NJ (US)

(*) Notice: Subject to any disclaimer, the term of this patent is extended or adjusted under 35 U.S.C. 154(b) by 0 days.

(21) Appl. No.: 14/313,636

(22) Filed: Jun. 24, 2014

(65) Prior Publication Data
US 2014/0378904 A1    Dec. 25, 2014

Related U.S. Application Data

(60) Provisional application No. 61/838,786, filed on Jun. 24, 2013.

(51) Int. Cl.
| A61B 17/34 | (2006.01) |
| A61M 5/158 | (2006.01) |
| A61M 25/01 | (2006.01) |
| A61M 5/32 | (2006.01) |
| A61M 5/42 | (2006.01) |
| A61M 5/46 | (2006.01) |
| A61B 17/00 | (2006.01) |

(52) U.S. Cl.
CPC ............ *A61B 17/3401* (2013.01); *A61M 5/158* (2013.01); *A61M 5/3293* (2013.01); *A61M 5/427* (2013.01); *A61M 5/46* (2013.01); *A61M 25/0102* (2013.01); *A61B 2017/00477* (2013.01); *A61M 2005/1587* (2013.01); *A61M 2205/13* (2013.01)

(58) Field of Classification Search
CPC ............ A61B 17/3401; A61B 17/3403; A61B 10/0283; A61B 2017/00477; A61M 5/158; A61M 25/0102; A61M 5/427; A61M 5/3293; A61M 5/46; A61M 2205/13

USPC .......... 604/167.01, 167.02, 164.01, 272, 256, 604/35

See application file for complete search history.

(56) References Cited

U.S. PATENT DOCUMENTS

| 2,866,453 A | 12/1958 | Jewett |
| 4,026,287 A | 5/1977 | Haller |
| 4,162,673 A | 7/1979 | Patel |
| 4,175,567 A | 11/1979 | Patel |
| 4,215,699 A | 8/1980 | Patel |

(Continued)

FOREIGN PATENT DOCUMENTS

| CN | 2571332 Y | 9/2003 |
| CN | 201328862 Y | 10/2009 |

(Continued)

OTHER PUBLICATIONS

Sawada et al., *Epidrum: a new device to identify the epidural space with an epidural Tuohy needle*, published online Nov. 13, 2011, J Anesth, Japanese Society of Anesthesiologists 2011.

(Continued)

*Primary Examiner* — Kami A Bosworth
*Assistant Examiner* — Hamza Darb
(74) *Attorney, Agent, or Firm* — Paul Diamond, Esq.; Diamond Law Office LLC (57) ABSTRACT

The invention provides improved apparatuses and related methods for the detection of needle penetration into negative pressure corporal spaces such as the epidural space. In one aspect, the invention provides a needle hub that includes a fluid reservoir chamber and a plunger engaged therewith, so that insertion of the plunger into the chamber displaces fluid causing a hanging drop to form.

16 Claims, 5 Drawing Sheets

(56) References Cited

U.S. PATENT DOCUMENTS

| | | | |
|---|---|---|---|
| 4,623,335 A * | 11/1986 | Jackson | 604/118 |
| 4,799,494 A * | 1/1989 | Wang | 600/566 |
| 4,801,293 A | 1/1989 | Jackson | |
| 4,940,458 A | 7/1990 | Cohn | |
| 5,024,655 A | 6/1991 | Freeman et al. | |
| 5,069,665 A | 12/1991 | Ng | |
| 5,084,016 A | 1/1992 | Freeman et al. | |
| 5,188,594 A | 2/1993 | Zilberstein | |
| 5,205,828 A | 4/1993 | Kedem | |
| 5,902,273 A * | 5/1999 | Yang et al. | 604/118 |
| 6,773,417 B2 | 8/2004 | Fitzgibbons et al. | |
| 7,175,608 B2 | 2/2007 | Hasan et al. | |
| 2004/0181192 A1 * | 9/2004 | Cuppy | 604/256 |
| 2004/0186430 A1 | 9/2004 | Hasan et al. | |
| 2007/0213688 A1 * | 9/2007 | Klein | 604/523 |

FOREIGN PATENT DOCUMENTS

| | | |
|---|---|---|
| CN | 202665704 U | 7/2012 |
| CN | 102614563 A | 8/2012 |
| CN | 202365879 U | 8/2012 |
| CN | 102715937 A | 10/2012 |
| CN | 202505895 U | 10/2012 |
| EP | 0608659 A1 | 8/1994 |
| WO | WO2011094957 | 8/2011 |

OTHER PUBLICATIONS

Finucane, *Complications of Regional Anesthesia* 2$^{nd}$ *Ed.*, Library of Congress Control No. 2006931197, © 2007 Springer Science+Business Media, LLC., 233 Spring Street, New York, NY 10013.

PCT/US2014/043955 International Search Report and Written Opinion of the ISA, mailed Nov. 4, 2014.

\* cited by examiner

APPARATUS FOR HANGING DROP DETECTION OF EPIDURAL SPACE PENETRATION

CROSS-REFERENCE TO RELATED APPLICATIONS

This application claims the benefit of U.S. provisional application Ser. No. 61/838,786 filed Jun. 24, 2013, which is hereby incorporated by reference in its entirety.

FIELD OF THE INVENTION

The invention relates to the field of epidural needles and anesthesia.

BACKGROUND OF THE INVENTION

Epidural anesthesia is a popular method of treating acute and chronic pain. Most commonly, the "loss of resistance" (LOR) technique has been used to detect needle penetration into the space. This technique involves connecting the needle, such as a Tuohy needle, via a needle hub to a syringe filled with saline solution and continuously pushing on the piston of the syringe while the needle is inserted toward the epidural space until a loss of resistance is encountered indicating that the needle tip has entered the space. An alternative method of detection is the "hanging drop" (HD) technique which relies on visualizing the aspiration of a small volume of fluid from the hub of the needle as the pressure at the needle tip decreases below atmospheric level upon entry into the epidural space. However, conventional application of the hanging drop technique is less than optimal due to the number of manipulations required while the needle is inserted in a patient.

What is needed and provided by the present invention are new and improved apparatuses and methods for detecting needle penetration into a negative pressure (subatmospheric) space such as the epidural space.

SUMMARY OF THE INVENTION

One embodiment of the invention provides a hub and needle apparatus for detecting penetration of the needle into a negative pressure space, such as the epidural space, which includes:

an elongate needle having a proximal end, a distal penetration end and a longitudinal axis, wherein a lumen extends lengthwise through the needle and opens at each end of the needle; and a hub assembly having a proximal end and a distal end, the hub assembly including:

a lumen formed by the hub assembly, a proximal end portion of the needle connected to the distal end of the hub assembly with the lumens of the needle and hub assembly in fluid communication with each other, a stylet port disposed at the proximal end of the hub assembly, the stylet port communicating with the lumen of the hub assembly and having a longitudinal axis which is coaxial with the longitudinal axis of the needle at the needle's proximal end;

a fluid reservoir chamber in communication with the lumen of the hub assembly; and a moveable plunger sealably engaging the fluid reservoir chamber.

The hub and needle apparatus may further include:

a fluid redirection member rotatably and removably connected to the stylet port of the hub assembly, the fluid redirection member having a lumen opening on one side into the lumen of the hub assembly when connected to the stylet port and opening to the exterior in a direction transverse to the longitudinal axis of the stylet port.

The hub and needle apparatus may further include:

a separate stylet that includes:

an elongate stylet member having a proximal end and a distal insertion end; and a stylet handle connected to the proximal end of the stylet member, the stylet handle including an outward-facing fluid connection port, wherein the stylet and the hub assembly are mutually sized and configured so that when the stylet is fully inserted into the hub assembly, the outward facing fluid connection port of the stylet is in fluid communication with the lumen of the hub assembly while fluid communication with the proximal opening of the elongate needle is blocked, and wherein the stylet is fully inserted into the hub assembly such that the outward facing fluid connection port of the stylet is in fluid communication with the lumen of the hub assembly and fluid communication with the proximal opening of the elongate needle is blocked.

The fluid reservoir chamber(s) may be at least substantially filled with liquid with the plunger disposed therein outwardly displaced from its fully inserted position so that it can be inserted to displace the liquid from the chamber.

The invention further provides kits that include a hub and needle apparatus of the invention along with a mutually sized and configured stylet for use therewith.

A still further embodiment of the invention provides a specialized stylet, which includes:

an elongate stylet member having a proximal end, a distal insertion end, a central longitudinal axis and an outer diameter; and a stylet handle having a proximal side and a distal side, the distal side of the stylet handle connected to the proximal end of the stylet member and the stylet handle including a proximally-facing fluid connection port forming a lumen, said lumen extending via a passage through to the distal side of the stylet handle, wherein the average exterior dimension of the stylet handle transverse to the central longitudinal axis of the elongate stylet member is greater than the outer diameter of the stylet member.

The invention also provides methods for detecting the penetration of a needle into a negative pressure space, such as the epidural space, and for inserting the needle therein, that employ the hub and needle apparatuses described herein.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

The invention provides improved hub and needle apparatuses for the detection of needle penetration into negative pressure spaces, such as the epidural space, by a hanging drop aspiration technique. In one aspect, the hubs of the invention include one or more fluid reservoir chambers each engaging a plunger, so that insertion of a plunger into a chamber displaces a fluid, such as saline, causing a hanging drop to form.

One embodiment of the invention provides a hub and needle apparatus for detecting penetration of the needle into a negative pressure space, such as the epidural space, which includes:
 an elongate needle having a proximal end, a distal penetration end and a longitudinal axis, wherein a lumen extends lengthwise through the needle and opens at each end of the needle; and
 a hub assembly having a proximal end and a distal end, the hub assembly including:
  a lumen formed by the hub assembly, a proximal end portion of the needle connected to the distal end of the hub assembly with the lumens of the needle and hub assembly in fluid communication with each other,
  a stylet port disposed at the proximal end of the hub assembly, the stylet port communicating with the lumen of the hub assembly and having a longitudinal axis which is coaxial with the longitudinal axis of the needle at the needle's proximal end;
  a fluid reservoir chamber in communication with the lumen of the hub assembly; and
  a moveable plunger sealably engaging (inserted in) the fluid reservoir chamber.

The hub and needle apparatus may further include:
 a fluid redirection member rotatably and removably connected to the stylet port of the hub assembly, the fluid redirection member having a lumen opening on one side into the lumen of the hub assembly when connected to the stylet port and opening to the exterior in a direction transverse to the longitudinal axis of the stylet port.

The hub and needle apparatus may further include:
 a separate stylet that includes:
  an elongate stylet member having a proximal end and a distal insertion end; and
  a stylet handle connected to the proximal end of the stylet member, the stylet handle including an outward-facing fluid connection port,
  wherein the stylet and the hub assembly are mutually sized and configured so that when the stylet is fully inserted into the hub assembly, the outward facing fluid connection port of the stylet is in fluid communication with the lumen of the hub assembly while fluid communication with the proximal opening of the elongate needle is blocked, and
  wherein the stylet is fully inserted into the hub assembly such that the outward facing fluid connection port of the stylet is in fluid communication with the lumen of the hub assembly and fluid communication with the proximal opening of the elongate needle is blocked.

The fluid reservoir chamber(s) may be at least substantially filled with liquid with the plunger disposed therein outwardly displaced from its fully inserted position so that it can be inserted to displace the liquid from the chamber.

The invention further provides kits that include a hub and needle apparatus of the invention along with a mutually sized and configured stylet for use therewith.

One embodiment of the invention provides a kit for detecting the penetration of a needle into a negative pressure space, such as the epidural space, which includes:
 (i) a hub and needle apparatus including:
  an elongate needle having a proximal end, a distal penetration end and a longitudinal axis, wherein a lumen extends lengthwise through the needle and opens at or near each end of the needle; and
  a hub assembly having a proximal end and a distal end, the hub assembly including:
   a lumen formed by the hub assembly, a proximal end portion of the needle connected to the distal end of the hub assembly with the lumens of the needle and hub assembly in fluid communication with each other,
   a stylet port disposed at the proximal end of the hub assembly, the stylet port communicating with the lumen of the hub assembly and having a longitudinal axis which is coaxial with the longitudinal axis of the needle at the needle's proximal end,
   a fluid reservoir chamber in communication with the lumen of the hub assembly, and
   a moveable plunger sealably engaging (inserted in) the fluid reservoir chamber; and
 (ii) a stylet including:
  an elongate stylet member having a proximal end and a distal insertion end; and
  a stylet handle connected to the proximal end of the stylet member, the stylet handle comprising an outward-facing fluid connection port,
  wherein the stylet and the hub assembly are mutually sized and configured so that when the stylet is fully inserted into the hub assembly, the outward facing fluid connection port of the stylet is in fluid communication with the lumen of the hub assembly while fluid communication with the proximal opening of the elongate needle is blocked.

The stylet may be preinserted into the hub and needle apparatus in the kit or it may be provided not inserted in the hub and needle apparatus, i.e., separate and apart, in the kit.

The kit may further include:
 a fluid redirection member sized and configured to rotatably and removably connect to the stylet port of the hub and needle assembly, the fluid redirection member having a lumen opening on one side into the lumen of the hub assembly when connected to the stylet port and opening to the exterior in a direction transverse to the longitudinal axis of the stylet port.

A still further embodiment of the invention provides a specialized stylet, which includes:
 an elongate stylet member having a proximal end, a distal insertion end, a central longitudinal axis and an outer diameter; and a stylet handle having a proximal side and a distal side, the distal side of the stylet handle connected to the proximal end of the stylet member and the stylet handle including a proximally-facing fluid connection port forming a lumen, said lumen extending via a passage through to the distal side of the stylet handle, wherein the average exterior dimension of the stylet handle transverse to the central longitudinal axis of the elongate stylet member is greater than the outer diameter of the stylet member.

The proximally-facing fluid connection port of the stylet handle may be secured to and fluidly connected with the distal end of a syringe, such as a saline filled syringe. The proximally-facing fluid connection port of the stylet handle may present a conically tapered recess for a tapered fit connection. For example, it may present a female Luer connector fitting. A syringe having a conically tapered protrusion connector (such as a corresponding male Luer fitting) sized and configured to form a tapered fit connection with the conically tapered recess presented by the stylet handle, may be reversibly connected to the stylet via the complementary tapers. Stylet handles having fluid communication between a proximal-side fluid connection port and the distal side of the stylet handle via one or more passages/holes may optionally have one or more one-way valves interposed therein, such as one-way micro-valves known in the art, permitting proximal to distal liquid flow.

Various aspects of the invention and its embodiments are still further described below with respect to the appended drawings.

Figure 1:
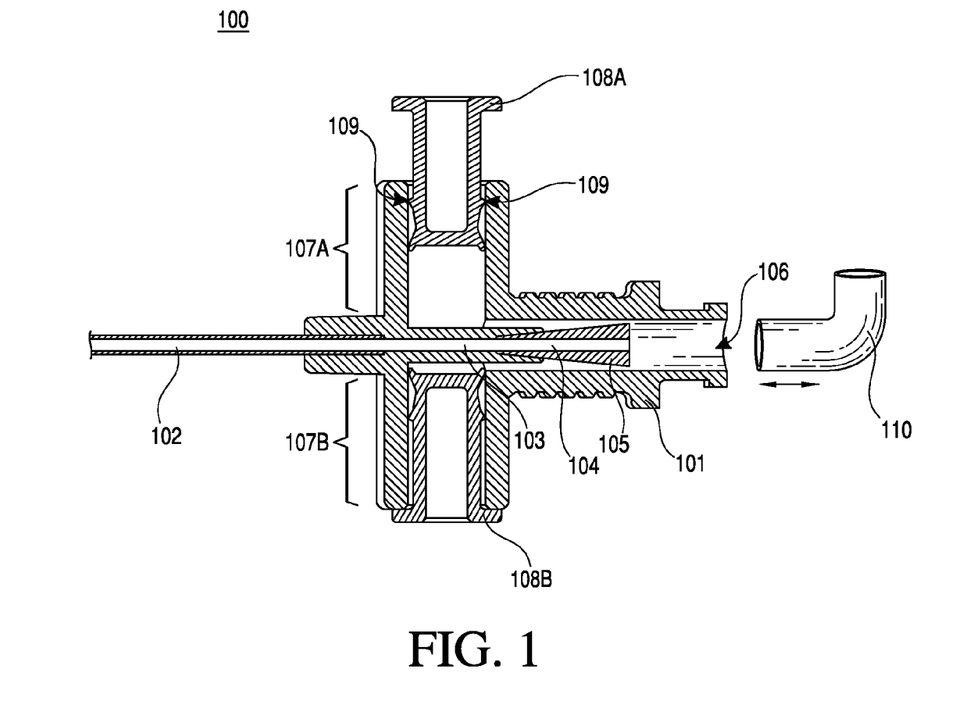
FIG. 1 schematically shows a longitudinal cross-section of a hub and needle embodiment of the invention.

FIG. 1 schematically shows a longitudinal cross-section of a hub and needle embodiment 100 of the invention that includes a hub 101, which is a type of manifold, and a hollow needle 102. The proximal end of needle 102 is securably inserted into and surrounded by the distal end of hub 101. The longitudinal lumen of needle 102 extends proximally into a longitudinal lumen section 103 formed by the hub and continues further proximally into longitudinal lumen section 104 formed by conical stylet seating portion 105 of the hub, eventually opening proximally into the proximal port (proximal stylet port) space 106 of hub 101. The inner dimension of proximal port 106 has a circular profile. Disposed transverse, here perpendicular, to the central longitudinal axes of the needle and hub are first and second opposing fluid reservoir chambers (barrels) 107A and 107B formed by hub 101 which outwardly open to the exterior but for plungers 108A and 108B inserted therein. Fluid reservoir chambers 107A and 107B are shown with a circular cross-sectional profile but may have any shaped profile so long as the plungers are mutually sized and configured. As shown for plunger 108A, each plunger may include a radially protruding circumferential seal 109. Alternatively, or in addition, the plunger(s) may user other type of annular seals such as O-ring seals, such as those known in the art. Plunger 108A is shown outwardly disposed while plunger 108B is shown fully inserted. Fluid redirection member 110 is a tubular elbow member sized and configured to slideably and rotatably (about the central longitudinal axis of hub 101) fit at one end into proximal port 106. As shown in the figure, the lumens formed between the end of the plungers and the respective fluid reservoirs chambers continue proximally into the interior space of the proximal stylet port portion of the hub.

Figure 2:
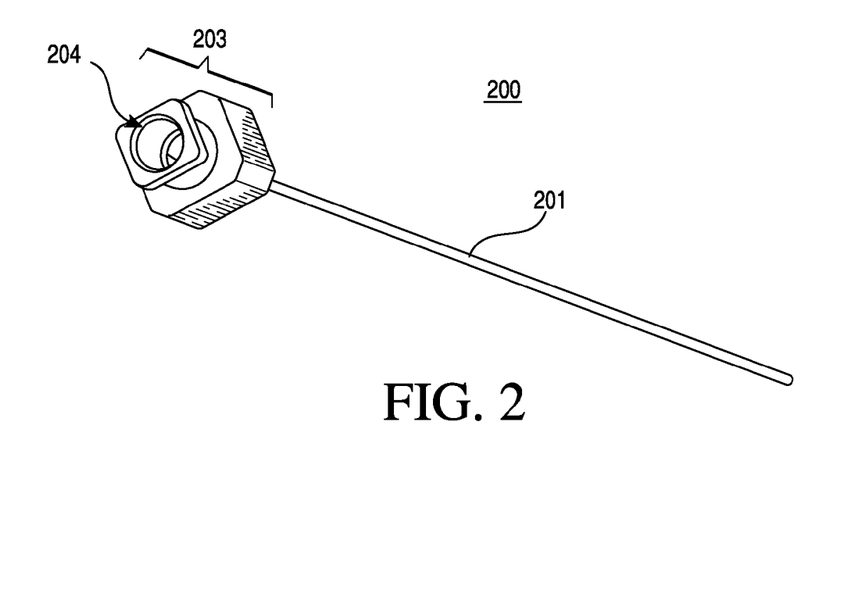
FIG. 2 shows a perspective view of stylet embodiment of the invention that may be used with the hub and needle embodiment shown in FIG. 1.

FIG. 2 shows a perspective view of a stylet embodiment of the invention 200 that may be used with the hub and needle embodiment shown in FIG. 1. Stylet 200 includes an elongated stylet member 201 connected at its proximal end to a stylet handle (cap) 203. The proximal end of stylet handle 203 forms and presents a connector 204, such as a Luer connector such as Luer slip or Luer lock type (female geometry shown) for connection to a mutually sized and configured syringe or other filling device.

Figure 3A:
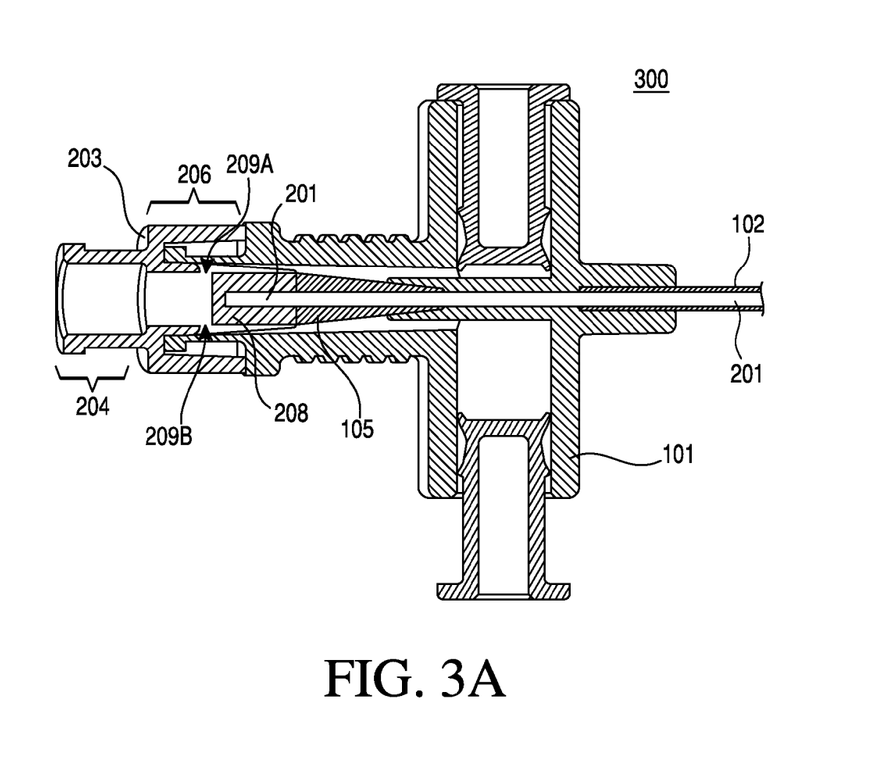
FIG. 3A schematically shows a longitudinal cross-section of the hub and needle embodiment shown in FIG. 1 with the mutually sized and configured stylet embodiment of FIG. 2 fully inserted and seated in the hub and needle apparatus.
Figure 3B:
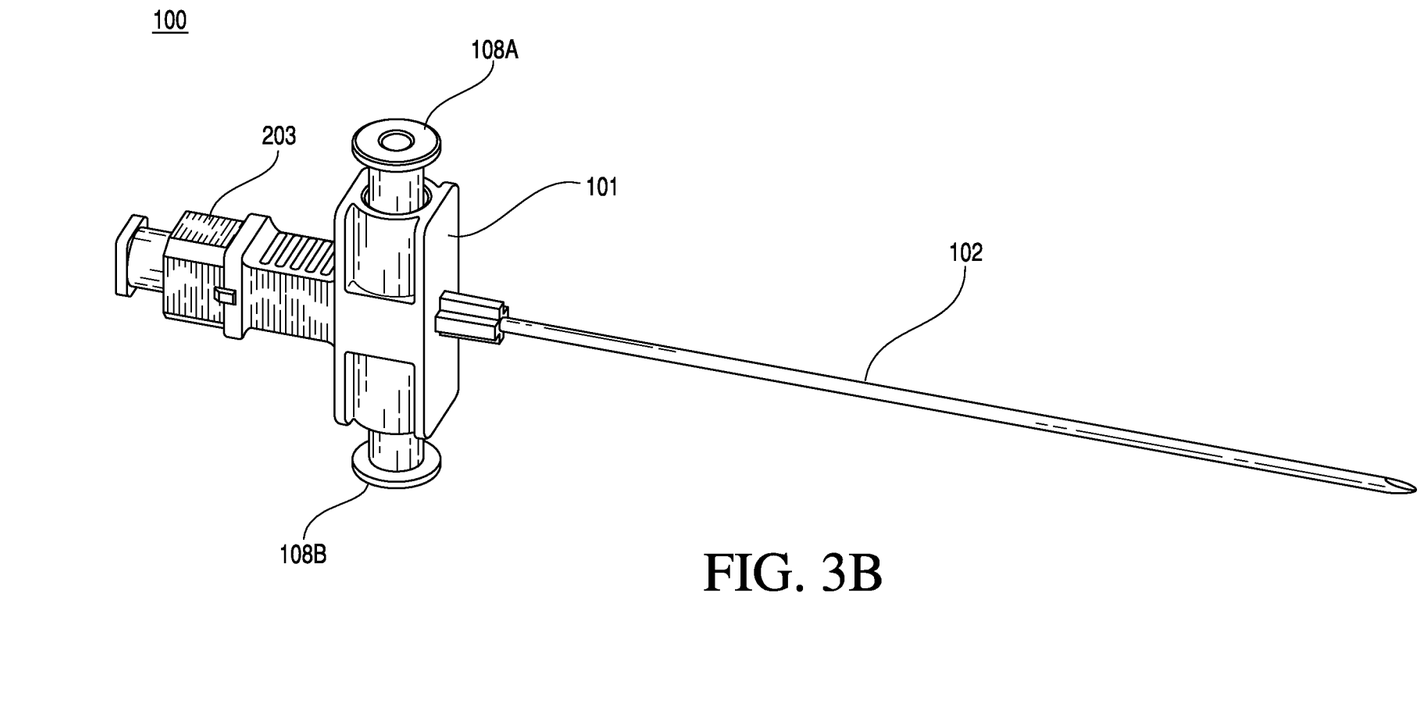
FIG. 3B shows an exterior perspective view of the hub and needle embodiment with the stylet inserted therein.

FIG. 3A schematically shows a longitudinal cross-section of the assembly 300 of the hub and needle embodiment shown in FIG. 1 with the mutually sized and configured stylet embodiment of FIG. 2 fully inserted into and seated in the hub and needle apparatus. The proximal end of elongate stylet member 201 is connected to the distal stylet connecting portion 208 of stylet handle 203. The outer radius of distal stylet connecting portion 208 of stylet handle 203 is not large enough to not block off the lumen that extends proximally from the fluid reservoir chambers. The distal-most portion of distal stylet connecting portion 208 is sized and configured to abut the proximal face of conical stylet seating portion 105 of hub 101. Portion 206 of stylet handle 203 sealingly surrounds the proximal stylet port portion of hub 101. Stylet handle 203 has formed therein one or more passageways, here two, 209A and 209B that fluidly connect the inner volume of connector portion 204 to the continuous lumen including and extending proximally from the fluid reservoir chambers of hub 101. FIG. 3B shows an exterior perspective view of the hub and needle embodiment with the stylet inserted therein.

The plungers shown in the figures are push plungers. Alternatively, one or more or all of the plungers could be screw plungers having threads that engage with corresponding internal threads of the fluid reservoir chamber such that the practitioner screw inserts the plunger(s) to displace the fluid in the chamber(s).

The invention also provides methods of preparing the apparatuses for use, methods for detecting the penetration of a needle into a negative pressure space, such as the epidural space, using the apparatuses and methods for inserting the needle into the space using the apparatuses.

The hub and needle apparatuses of the invention may, for example, be provided by the manufacturer for use in sterile form prefilled with saline with the one or more plungers displaced outwardly from their fully inserted positions, ready to be pressed inward (or otherwise advanced inward) during the procedure to obtain the hanging drop. In the case that the hub and needle apparatuses are provided prefilled, a stylet may also be pre-inserted. In this case, the stylet may be a conventional stylet (without a proximal end connection port communicating with the distal side of the stylet handle) or it may be the manner of stylet described herein which presents a proximal end connection port (for connection to a syringe) having a lumen in fluid communication with the distal side of the stylet handle and hub assembly lumen when the stylet is inserted into the hub and needle apparatus. If the hub and needle apparatus is supplied with the latter manner of stylet preinserted, the proximal port of the stylet handle may be closed with a cap/plug, such as a removable cap/plug, sized and configured to sealably engage the port. For example, if the stylet port presents a female Luer connector, the cap may present a complementary solid conical (or frusto-conical) protrusion on one end and a tap (for grabbing and removing the cap/plus) on the other end.

Figures 4A, 4C:
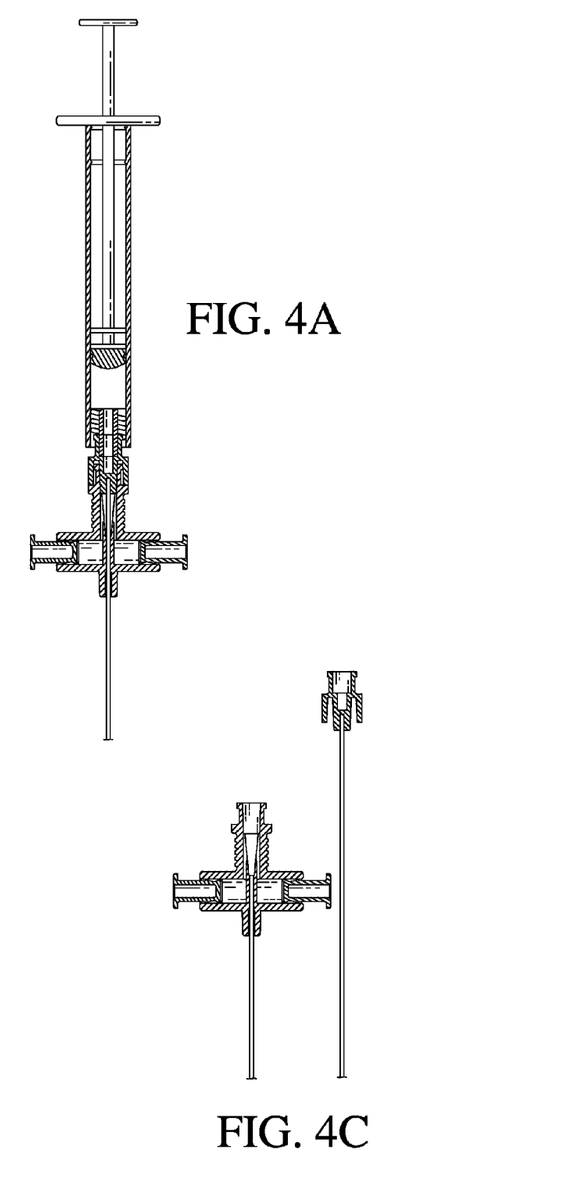
FIGS. 4A-D schematically show in longitudinal cross-sections steps in preparing and using the embodiments shown in FIGS. 1-3 for the detection of needle penetration into the epidural space.

Alternatively, the hub and needle apparatus may be supplied dry, i.e., unfilled with saline or other liquid, to be filled for use by the anesthesia personnel prior to use. The hub and needle apparatus may be supplied with the stylet having the proximal port in fluid communication with its distal side already fully inserted into the hub and needle apparatus. The proximal port of the stylet may or may not be provided with a cap/plug reversibly closing it. When the hub and needle apparatus is provided dry, the one or more plungers may be provided in a closed (fully inserted position), an open position or an intermediate position. The filling of the hub and needle apparatus with inserted stylet (having a proximal port in fluid communication with the distal end of the stylet handle) using a saline filled syringe is shown in FIG. 4A. The plunger(s) may be initially disposed in a fully inserted position and be displaced outwardly as pressure form the syringe fills the fluid reservoir chambers. This method minimizes the air trapped in the syringe that needs to escape during filling. It should also be understood that the lumen of the hub assembly may also be filled under a vacuum/partial vacuum.

Figure 4B:
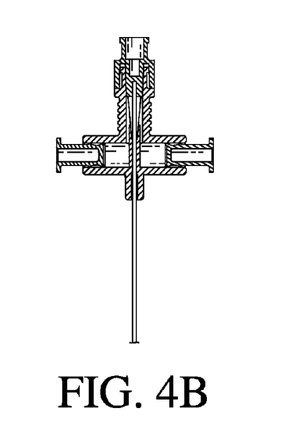

The syringe is thereafter removed and the filled hub and needle apparatus with inserted stylus remaining is then inserted to just outside the epidural space (FIG. 4B), such as in a typical epidural procedure. In more detail, the epidural needle is inserted into the ligamentum flavum. Anatomical structures traversed include skin, subcutaneous tissue, supraspinous ligament, and interspinous ligament. In the lumbar area, the depth of skin to ligamentum flavum is approximately 4 cm for most adults. Eighty percent of adults have a skin to ligamentum flavum depth of 3.5-6 cm. The average thickness of the ligamentum flavum is 5-6 mm. Controlling the needle is important to avoid a dural puncture. In the thoracic area, needle control is important to avoid dural puncture and risk of spinal cord injury.

Figure 4D:
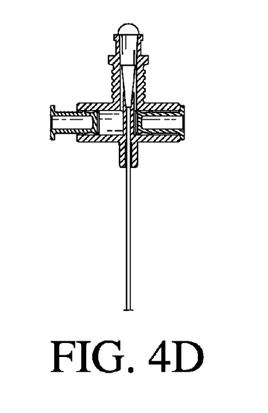

Once the epidural needle of the apparatus is just outside the epidural space, the stylet is carefully withdrawn and set aside (FIG. 4C). At this point, depending on the orientation of the patient undergoing the procedure, a fluid redirection member (e.g. an elbow tube) may be connected to the stylet port of the hub assembly to ensure that the hanging drop to be formed will be in an at least substantially upright position. One of the plungers of the apparatus is then depressed to displace the saline in the reservoir chamber to create (bring up) a hanging drop at the proximal stylet port of the hub (FIG. 4D). The needle is then carefully advanced further toward the epidural space until aspiration of the hanging drop indicates that the distal end of the needle has entered the epidural space. In this manner, the anesthesia practitioner does not need to remove their hands from the apparatus to fill the hub with another syringe in order to obtain the hanging drop during the procedure as they would using a conventional hanging drop technique. In addition, since the embodiment shown in FIGS. 4A-D is a two-plunger apparatus, should the first hanging drop formed be inadvertently lost or aspirated due to a false positive drop in pressure, the practitioner can simply depress the second plunger to form a new hanging drop. Each plunger may also be capable of setting up more than one hanging drops depending on the volume of the fluid reservoir chamber.

Once the penetration of the needle into the epidural space is established, fine tuning of the needle position may optionally be performed according to practitioner preference and a catheter may be inserted through the needle into the epidural space for delivery of anesthesia and/or other medicaments.

While the apparatuses of the present invention are advantageously adapted to carry out the manner of hanging drop technique described herein, they may also be used in a variation of the loss of resistance technique by applying constant inward pressure to one or more plungers after the stylet is removed and while the needle is advanced toward the epidural space, until loss of resistance is sensed on the plunger(s) indicating penetration of the distal tip of the needle into the epidural space. In this case, a cap or plug may be secured to the stylet port of the hub assembly after the style is removed and prior to the advance in order to seal pressure within the lumen of the needle hub. This loss of resistance method may, for example be performed with the lumen of the needle hub only air/gas filled (or at least substantially air/gas filled) or liquid filled, such as saline filled. The loss of resistance method is not sensitive to the orientation of the patient during the procedure.

Figure 5:
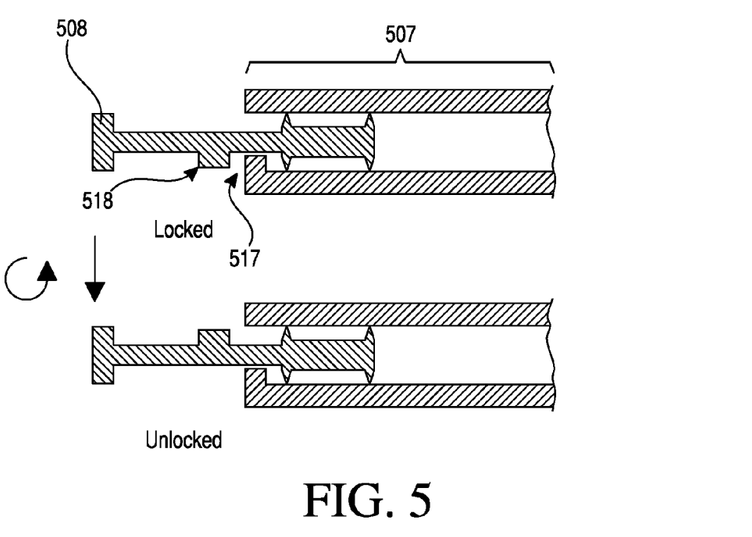
FIG. 5 schematically shows a safety mechanism that may be built into the hub and needle apparatuses to prevent inadvertent depression of a push plunger.

FIG. 5 schematically shows a safety mechanism that may be built into the hub and needle apparatuses to prevent inadvertent depression of a push plunger. FIG. 5 (top) shows fluid reservoir chamber 507 of a hub and needle apparatus similar to that shown in FIG. 1 except that a nub 517 extends radially inward from only part of the circumference of the wall of the chamber. The shaft of plunger 508 presents a radially outward extending nub 518. When the nubs are circumferentially coaligned, nub 517 blocks nub 518 preventing the plunger from depressing. When the plunger is rotated about the central axis of the plunger so that the paths of nubs 517 and 518 no longer overlap (FIG. 5 bottom), the plunger may be depressed. Before the needle is inserted into a patient, the apparatus may be provided in the locked position and switched to the unlocked position by rotating the plunger when the practitioner desires to form the hanging drop.

Figure 6A:
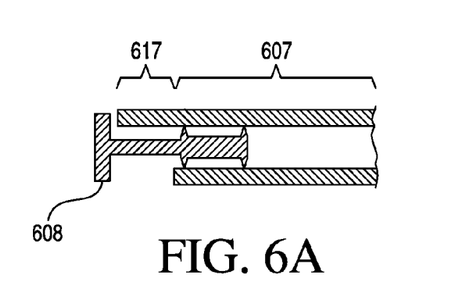
FIGS. 6A and 6B schematically show another safety mechanism that may be built into the hub and needle apparatuses to prevent inadvertent depression of a push plunger.
Figure 6B:
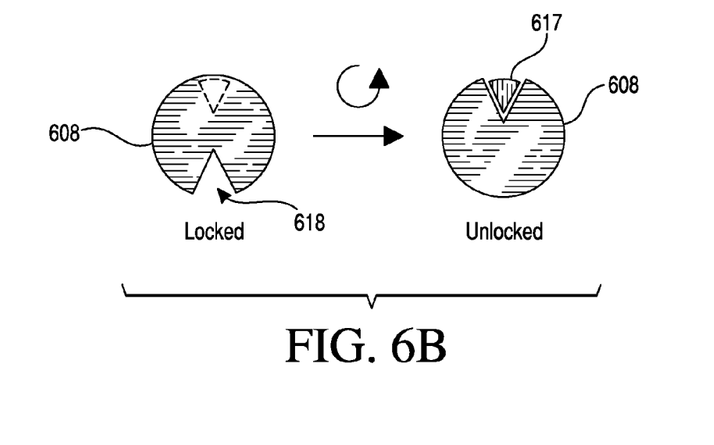

FIGS. 6A and 6B schematically show another safety mechanism that may be built into the hub and needle apparatuses to prevent inadvertent depression of a push plunger. FIG. 6A is a cross-sectional side view of a plunger inserted in a reservoir chamber of a hub embodiment of the invention. FIG. 6B is an end-on view. Here, a partial circumferential section 617 of fluid reservoir chamber 607 extends farther outward than the rest of the chamber. The press top of plunger 608 is configured with a cutout sized and configured to permit section 617 to pass upon depressing the plunger when the cutout and section 617 are circumferentially coaligned and to block the plunger when not coaligned. Again, before the needle is inserted into a patient, the apparatus may be provided in the locked position and switched to the unlocked position by rotating the plunger when the practitioner desires to form the hanging drop.

Thus, as exemplified in FIGS. 5 and 6A-B, where the plunger is a push plunger having a central longitudinal axis, the plunger and hub may be mutually sized and configured to selectively permit depression of the plunger based on the rotational position of the plunger about its central rotational axis.

The needle component of the hub and needle apparatuses of the invention may have any suitable configuration. For example, suitable types of needles for performing epidural procedures include the Tuohy needle, the Crawford needle and the Whitacre needle. Needle sizes are well known in the art and selection may vary, for example, based on age of the patient (child or adult). In general, 16-20 gauge needles may be used.

The various components of the invention may be made of any suitable materials. For example, the hub and stylet handle may be made from a medical grade polymer such as a polyethylene, polypropylene or acrylic. Alternatively, the hub and stylet handle may be metallic. The needle of the hub and needle apparatus may be metallic such as made from a stainless steel. The elongate stylet member may be metallic or polymeric. Both polymeric and metallic components may be manufactured using means well known in the art such as molding, injection molding, machining, welding, joining with adhesives and combinations thereof. Various components such as the hub and stylet handle may also be manufactured using three-dimensional (3D) printing techniques, as known in the art.

In any of the embodiments, the fluid redirection member and/or at least the stylet port portion of the hub body may be transparent to facilitate visualization of the aspiration of the hanging drop and column of liquid beneath it upon penetration of the epidural space.

Each of the patent applications, patents and other publications cited in this disclosure is incorporated by reference as if fully set forth herein. Although the invention has been described in connection with specific preferred embodiments, it should be understood that the invention as claimed should not be unduly limited to such specific embodiments.

What is claimed is:

1. A hub and needle apparatus for detecting penetration of the needle into a negative pressure space, comprising:
    an elongate needle having a proximal end, a distal penetration end and a longitudinal axis, wherein a lumen extends lengthwise through the elongate needle and opens at each end of the elongate needle, wherein the elongate needle is a hollow needle of the hub and needle apparatus; and
    a hub assembly having a proximal end and a distal end, the hub assembly comprising:
        a lumen formed by the hub assembly, a proximal end portion of the elongate needle connected to the distal end of the hub assembly with the lumens of the elongate needle and hub assembly in fluid communication with each other,
        a stylet port disposed at the proximal end of the hub assembly, the stylet port communicating with the lumen of the hub assembly and having a longitudinal axis which is coaxial with the longitudinal axis of the elongate needle at the elongate needle's proximal end;
        a fluid reservoir chamber in communication with the lumen of the hub assembly, wherein said communication is not via the stylet port; and
        a manually moveable plunger sealably engaging the fluid reservoir chamber, wherein the plunger is a push plunger or a screw plunger.

2. The hub and needle apparatus of claim 1, further comprising:
    a fluid redirection member rotatably and removably connected to the stylet port of the hub assembly, the fluid redirection member having a lumen opening on one side into the lumen of the hub assembly when connected to the stylet port and opening to the exterior in a direction transverse to the longitudinal axis of the stylet port.

3. The hub and needle apparatus of claim 1, further comprising:
    a separate stylet comprising:
        an elongate stylet member having a proximal end and a distal insertion end; and
        a stylet handle having a proximal side and a distal side, the distal side of the stylet handle connected to the proximal end of the stylet member, the stylet handle comprising a proximally facing fluid connection port,
    wherein the stylet and the hub assembly are mutually sized and configured so that when the stylet is fully inserted into the hub assembly, the elongate stylet member of the stylet extends into the lumen of the elongate needle and the proximally facing fluid connection port of the stylet is in fluid communication with the lumen of the hub assembly while fluid communication with the proximal opening of the elongate needle is blocked,
    wherein the stylet and the hub assembly are mutually sized and configured so that the stylet is fully removable from the hub assembly after having been inserted therein, and wherein the stylet is fully inserted into the hub assembly such that the elongate stylet member of the stylet extends into the lumen of the elongate needle and the proximally facing fluid connection port of the stylet is in fluid communication with the lumen of the hub assembly while fluid communication with the proximal opening of the elongate needle is blocked.

4. The hub and needle apparatus of claim 1, wherein:
    the fluid reservoir chamber is at least substantially filled with liquid, and
    the plunger is outwardly displaced from its fully inserted position.

5. The hub and needle apparatus of claim 3, wherein:
    the fluid reservoir chamber is at least substantially filled with liquid, and
    the plunger is outwardly displaced from its fully inserted position.

6. The hub and needle apparatus of claim 1, comprising:
    two fluid reservoir chambers in communication with the lumen of the hub assembly; and
    for each of the two fluid reservoir chambers, a manually moveable plunger sealably engaging the fluid reservoir chamber.

7. The hub and needle apparatus of claim 6, wherein:
    the two fluid reservoir chambers are disposed about the hub in a laterally opposing configuration.

8. The hub and needle apparatus of claim 1, wherein the plunger is a push plunger having a central longitudinal axis and the plunger and hub are mutually sized and configured to selectively permit depression of the plunger based on the rotational position of the plunger about its central rotational axis.

9. The hub and needle apparatus of claim 1, wherein the lumen of the elongate needle is unobstructed and the stylet port is not closed.

10. The hub and needle apparatus of claim 1, wherein the hub assembly comprises:
    a hub member comprising:
        a lumen formed by the hub member, a proximal end portion of the elongate needle connected to the distal end of the hub member with the lumens of the elongate needle and the hub member in fluid communication with each other,
        a stylet port disposed at the proximal end of the hub member, the stylet port communicating with the lumen of the hub member and having a longitudinal axis which is coaxial with the longitudinal axis of the elongate needle at the elongate needle's proximal end, and
        a fluid reservoir chamber in communication with the lumen of the hub member, wherein said communication is not via the stylet port and wherein the fluid reservoir chamber is an integral part of the hub member; and
    a manually moveable plunger sealably engaging the fluid reservoir chamber, wherein the plunger is a push plunger or a screw plunger.

11. The hub and needle apparatus of claim 1, wherein the hub and needle apparatus consists essentially of:
    an elongate needle having a proximal end, a distal penetration end and a longitudinal axis, wherein a lumen extends lengthwise through the elongate needle and opens at each end of the elongate needle, wherein the elongate needle is a hollow needle of the hub and needle apparatus; and
    a hub assembly having a proximal end and a distal end, the hub assembly comprising:
        a lumen formed by the hub assembly, a proximal end portion of the elongate needle connected to the distal end of the hub assembly with the lumens of the elongate needle and hub assembly in fluid communication with each other, a stylet port disposed at the proximal end of the hub assembly, the stylet port communicating with the lumen of the hub assembly and having a longitudinal axis which is coaxial with the longitudinal axis of the elongate needle at the elongate needle's proximal end;

at least one fluid reservoir chamber in communication with the lumen of the hub assembly, wherein said communication is not via the stylet port; and for each fluid reservoir chamber, a manually moveable plunger sealably engaging the fluid reservoir chamber, wherein the plunger is a push plunger or a screw plunger.

12. A kit for detecting the penetration of a needle into a negative pressure space, comprising:

(i) a hub and needle apparatus comprising:

an elongate needle having a proximal end, a distal penetration end and a longitudinal axis, wherein a lumen extends lengthwise through the elongate needle and opens at or near each end of the elongate needle, wherein the elongate needle is a hollow needle of the hub and needle apparatus; and a hub assembly having a proximal end and a distal end, the hub assembly comprising:

a lumen formed by the hub assembly, a proximal end portion of the elongate needle connected to the distal end of the hub assembly with the lumens of the elongate needle and hub assembly in fluid communication with each other, a stylet port disposed at the proximal end of the hub assembly, the stylet port communicating with the lumen of the hub assembly and having a longitudinal axis which is coaxial with the longitudinal axis of the elongate needle at the elongate needle's proximal end, a fluid reservoir chamber in communication with the lumen of the hub assembly, wherein said communication is not via the stylet port, and a manually moveable plunger sealably engaging the fluid reservoir chamber, wherein the plunger is a push plunger or a screw plunger; and (ii) a stylet comprising:

an elongate stylet member having a proximal end and a distal insertion end; and a stylet handle connected to the proximal end of the stylet member, the stylet handle comprising an outward-facing fluid connection port, wherein the stylet and the hub assembly are mutually sized and configured so that when the stylet is fully inserted into the hub assembly, the elongate stylet member of the stylet extends into the lumen of the elongate needle and the outward facing fluid connection port of the stylet is in fluid communication with the lumen of the hub assembly while fluid communication with the proximal opening of the elongate needle is blocked, and wherein the stylet and the hub assembly are mutually sized and configured so that the stylet is fully removable from the hub assembly after having been inserted therein.

13. The kit of claim 12, further comprising:

a fluid redirection member sized and configured to rotatably and removably connect to the stylet port of the hub and needle assembly, the fluid redirection member having a lumen opening on one side into the lumen of the hub assembly when connected to the stylet port and opening to the exterior in a direction transverse to the longitudinal axis of the stylet port.

14. The kit of claim 12, wherein the hub and needle apparatus comprises:

two fluid reservoir chambers in communication with the lumen of the hub assembly; and for each of the two fluid reservoir chambers, a manually moveable plunger sealably engaging the fluid reservoir chamber.

15. The kit of claim 14, wherein:

the two fluid reservoir chambers are disposed about the hub in a laterally opposing configuration.

16. The kit of claim 12, wherein the plunger is a push plunger having a central longitudinal axis and the plunger and hub are mutually sized and configured to selectively permit depression of the plunger based on the rotational position of the plunger about its central rotational axis.

* * * * *